United States Patent [19]

Higgins et al.

[11] Patent Number: 5,971,935
[45] Date of Patent: Oct. 26, 1999

[54] METHODS AND APPARATUS FOR REDUCING NOISE IN SYSTEMS USING THERMISTOR CATHETERS TO MEASURE BIOLOGICAL FUNCTIONS

[75] Inventors: Michael J. Higgins, Trabuco Canyon; Luong N. Phan, Laguna Nigel, both of Calif.

[73] Assignee: Baxter International Inc., Deerfield, Ill.

[21] Appl. No.: 09/071,815

[22] Filed: May 1, 1998

[51] Int. Cl.$^6$ .................................................. A61B 5/028
[52] U.S. Cl. ............................................................ 600/526
[58] Field of Search ..................................... 600/549, 526

[56] References Cited

U.S. PATENT DOCUMENTS

| | | | |
|---|---|---|---|
| 3,766,908 | 10/1973 | Haynes ..................................... | 600/549 |
| 4,350,168 | 9/1982 | Chable et al. ........................... | 600/549 |
| 5,056,048 | 10/1991 | Seperant .................................. | 600/549 |

OTHER PUBLICATIONS

Baxter Product Brochure *"Thermodilution Cardiac Output Computer Technique Model COM–1™."* Apr. 1984.
Baxter Product Brochure *"Connecting Cable and Accessories for the Model COM–1 Cardiac Output Computer."* Apr. 1984.
Baxter Product Brochure *"COM–2™ Performance You Can Trust"* Nov. 1988.
Baxter Product Brochure *"A New way to evaluation the 'other' heart. REF.–1™"* Apr. 1989.
Baxter Product Brochure *"Explorer™. The More Complete Picture."* Apr. 1992.
Baxter Product Brochure *"HP Vue Link and Baxter's Explorer™ and Vigilance® Monitors. Bringing It All Together"* Oct. 1993.
Baxter Product Brochure *"SAT–2™, An important event in $SvO_2$ monitoring."* Aug. 1989.

*Primary Examiner*—William E. Kamm
*Attorney, Agent, or Firm*—Eric K. Satermo; Guy L. Cumberbatch

[57] ABSTRACT

A system for measuring biological functions of a patient, such as cardiac output, filters noise from a signal provided by a thermistor catheter inserted into the body of the patient. A signal-conditioning cable is disposed between the catheter and an instrument which processes the signal to measure cardiac output. The cable includes circuitry which forms, in combination with a thermistor of the catheter, a low-pass filter for attenuating thermal and high-frequency noise from the signal provided to the instrument. The instrument can more accurately measure cardiac output with the filtered signal than with an unfiltered signal. Although the circuitry which forms the low-pass filter may be combined with the catheter or the instrument, it is preferred to dispose the circuitry in a separate cable to reduce manufacturing costs of the catheter and retrofitting costs of existing instruments.

18 Claims, 3 Drawing Sheets

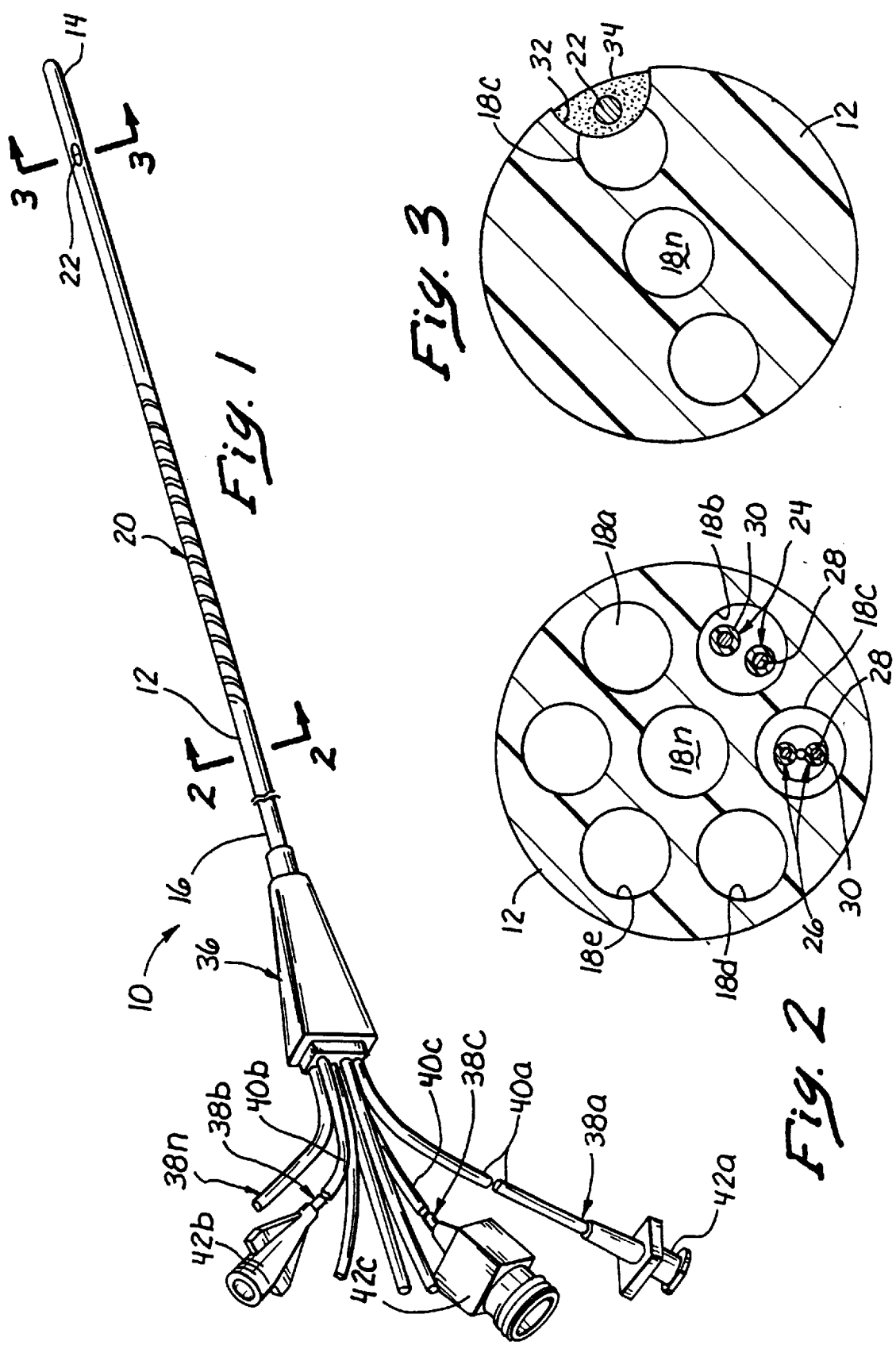

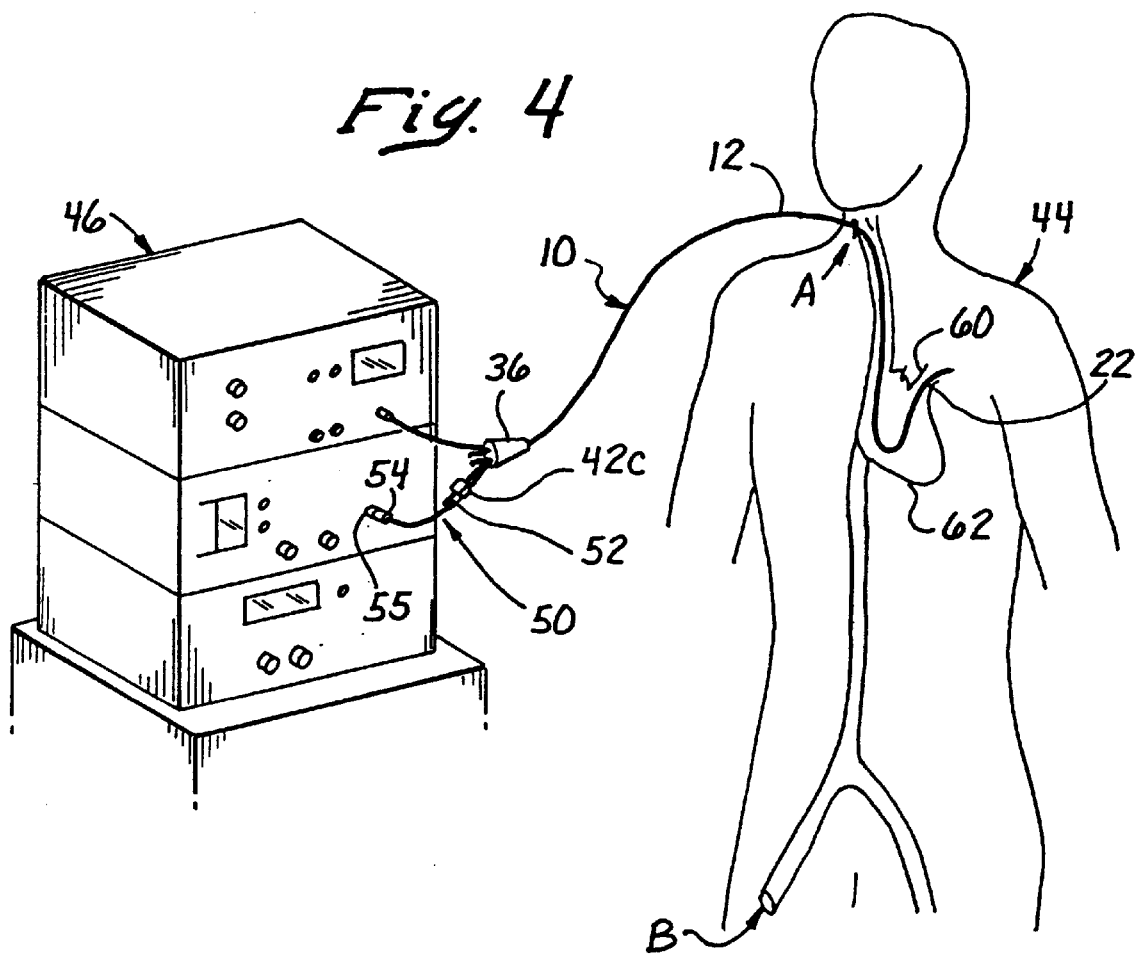
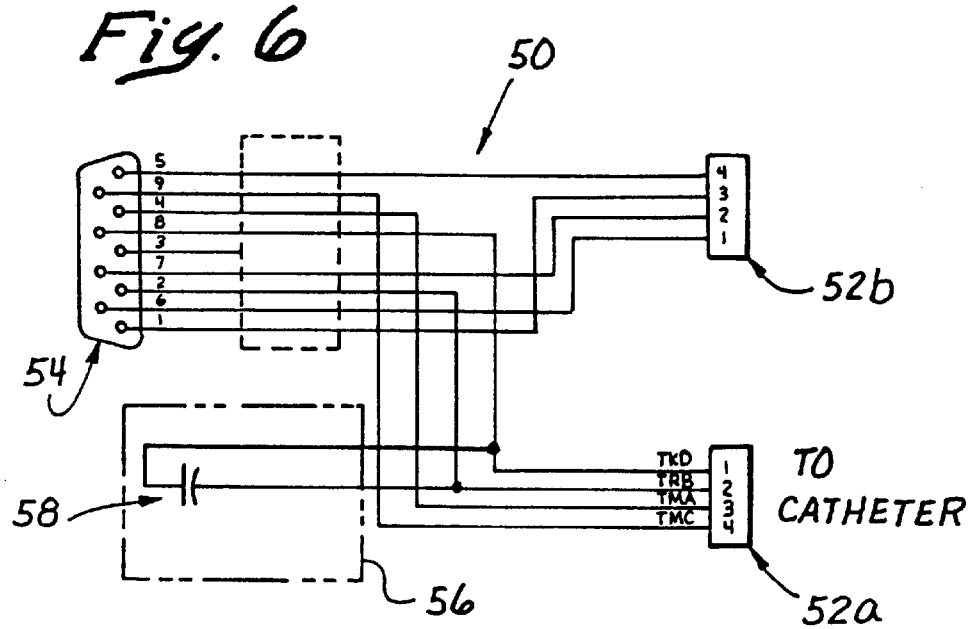

METHODS AND APPARATUS FOR REDUCING NOISE IN SYSTEMS USING THERMISTOR CATHETERS TO MEASURE BIOLOGICAL FUNCTIONS

BACKGROUND OF THE INVENTION

1. Field of the Invention

The present invention relates to systems for measuring biological functions of a patient and, more particularly, to systems which use a thermistor catheter to measure biological functions continuously. The present invention also relates to methods and apparatus for reducing noise in a signal provided by a thermistor catheter to a processing instrument so that the instrument may more accurately measure biological functions such as cardiac output. The present invention is particularly beneficial in environments in which large amounts of thermal and/or high-frequency noise are present.

2. Description of the Related Art

Biological functions of a patient, particularly cardiac functions such as intercardiac pressure, flow rate, and ejection fraction, are monitored by physicians in order to obtain vital information necessary to perform various cardiovascular procedures. Of the various cardiac functions, cardiac output indicates to a physician the amount or volume of blood pumped by the heart per unit time. Information on a patient's cardiac output indicates the effectiveness of the heart as a pump and of blood circulation.

Cardiac output may be measured continuously throughout a particular surgical procedure. The cardiac output of a patient may also be measured before and after a surgical procedure. To measure cardiac output, the physician inserts a catheter into the cardiovascular system and positions the catheter at a target sight. The catheter has a heating element which is activated to heat the blood flowing around the catheter at the target sight. A temperature sensor, for example, a thermistor, positioned downstream of the heating element provides a signal from which blood temperature is calculated. Cardiac output may then be calculated based upon the blood temperature in conjunction with other variables.

The signal from the temperature sensor is relatively small. Accordingly, conventional temperature-sensing catheters are vulnerable to a number of error-inducing sources. A surgical theater is a particularly noisy electrical environment, due in part to multiple machines operating simultaneously. The human body is also very noisy. All of this electronic, thermal, and physiological noise decreases the accuracy of the signal from the temperature sensor and, therefore, affects the accuracy of cardiac output measurements and hinders a physician's ability to successfully diagnose, monitor, and treat cardiovascular problems of a patient. Although sophisticated signal-processing techniques and equipment have been employed in the prior art to reduce the amount of noise (and resultant error) as much as possible, there still exists a significant amount of noise in the measurement of cardiac output.

Conventional signal-processing techniques are implemented either on the catheter itself or in the processing instrumentation. As catheters are discarded after a single use, it is not cost effective to include signal-processing circuitry on the catheter. Such implementation increases the cost of the catheter and is wasteful as the catheter and the circuitry are disposed of after one use. Alternatively, the circuitry may be incorporated in the processing instrumentation. However, there are thousands of existing instruments in use which become obsolete and need to be replaced in view of new instruments including signal-processing circuitry. This is also expensive and wasteful.

Errors may also be introduced into the measurement of cardiac output when a thermal time response of the thermistor is fast. The thermal time response of a thermistor indicates how quickly the thermistor reacts to changes in temperature. One method attempting to overcome introduced errors is to control the time response of the thermistor by adding or subtracting material on the catheter at the thermistor. The amount of material controls the thermal time response mechanically. More material results in lower thermal diffusion, and less material results in higher thermal diffusion. One of the drawbacks of this approach is that it is expensive, particularly on disposable catheters. In addition, it is difficult to control the time response consistently with this mechanical approach.

BRIEF SUMMARY OF THE INVENTION

In view of the foregoing drawbacks of convention techniques in measuring cardiac output, one of the objectives of the present invention is to provide methods and apparatus for measuring biological functions, for example, cardiac output, accurately in environments in which thermal and/or high-frequency noise is present.

It is an additional object of the present invention to provide methods and apparatus for reducing noise in a signal provided by a catheter to processing instrumentation for measuring biological functions in a cost-effective manner.

It is yet another object of the present invention to provide methods and apparatus for filtering noise from a signal provided by a catheter to processing instrumentation to reduce errors in measuring biological functions.

According to one aspect of the invention, a system for monitoring biological functions of a patient, such as cardiac output, includes a catheter connected to processing instrumentation by a signal-conditioning cable. The catheter includes a temperature sensor disposed at or near a distal end thereof which provides a signal indicative of changes in temperature in the patient. The signal-conditioning cable includes circuitry which conditions the signal from the temperature sensor. For example, the circuitry may include a capacitor which filters noise from the signal. The processing instrumentation then receives the conditioned signal from the signal-conditioning cable for processing to determine particular biological functions, for example, cardiac output.

One of the advantages of the present invention is that existing catheters and processing instrumentation may be used in conjunction with the signal-conditioning cable. Accordingly, the cost of the manufacturing the catheters is not increased by implementing signal-processing circuitry therein, and the cost of retrofitting existing instrumentation with signal-processing circuitry is eliminated. In addition, the lifetime of existing processing instrumentation is increased as these instruments are not rendered obsolete.

In accordance with another aspect of the invention, the temperature sensor of the catheter may include a thermistor, which is a resistive element. The circuitry of the signal-conditioning cable may then include a capacitor. The circuitry is configured such that the capacitor forms a filtering circuit with the thermistor when the cable is connected to the catheter. Accordingly, as the cable utilizes the resistive function of the thermistor, additional resistors do not need to be included in the circuitry of the signal-conditioning cable, which reduces the manufacturing costs.

The circuitry of the signal-conditioning cable may be configured as a low-pass filter. For example, the circuitry may attenuate frequencies greater than about 1 Hertz (Hz). Accordingly, any thermal noise and high-frequency noise which may be present in the signal provided by the temperature sensor is substantially eliminated. As such, the signal provided to the processing instrumentation is substantially free from noise so that cardiac output may be accurately measured.

The signal-conditioning cable may include any type of input connector for coupling with any type of catheter and may include any type of output connector for coupling with any type of existing processing instrumentation. The cable is preferably flexible for easy implementation and maneuverability. In addition, the signal-conditioning cable may be reusable for multiple procedures and with multiple catheters and instrumentation.

Other objects, features, and advantages of the present invention will become apparent to those skilled in the art from a consideration of the following detailed description taken in conjunction with the accompanying drawings which illustrate, by way of example, the principles of the present invention in the context of a system for measuring cardiac output, but which are equally relevant to systems which measure other biological and cardiac functions with a catheter.

BRIEF DESCRIPTION OF THE SEVERAL VIEWS OF THE DRAWINGS

FIG. 1 is a perspective view of a catheter configured for sensing temperature in accordance with the present invention;

FIG. 2 is a cross-sectional view of the catheter of the invention, taken along line 2—2 of FIG. 1, particularly illustrating multiple lumens;

FIG. 3 is a cross-sectional view of the catheter taken along line 3—3 of FIG. 1, particularly illustrating a temperature sensor;

FIG. 4 is a perspective view of a system for monitoring biological functions of a patient in accordance with the present invention, particularly illustrating a signal-conditioning cable connecting a temperature-sensing catheter to processing instrumentation;

FIG. 6 is a schematic view of an exemplary signal-conditioning cable in accordance with the present invention.

DETAILED DESCRIPTION OF THE INVENTION

Figure 5:
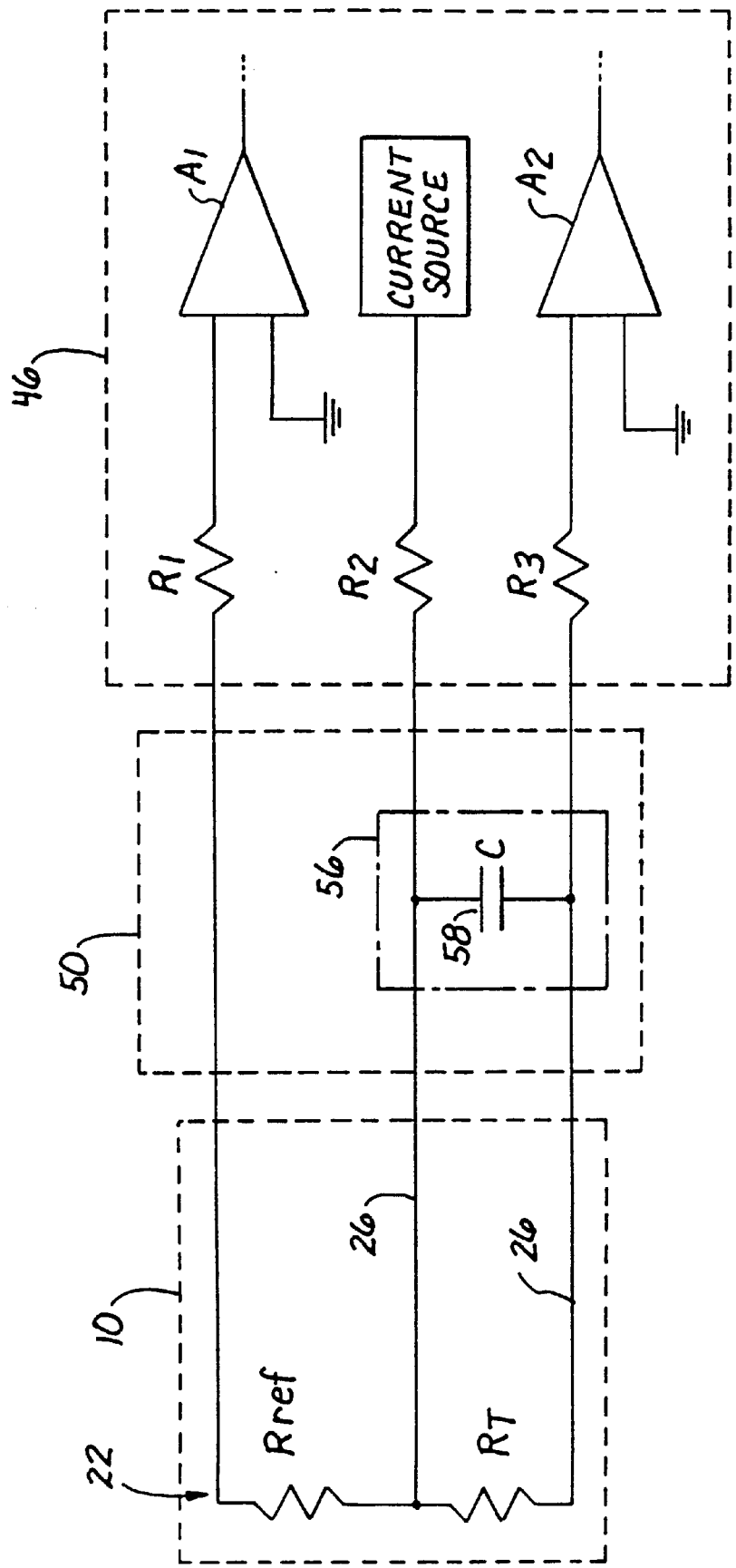
FIG. 5 is a schematic view of the system for monitoring biological functions of the invention, particularly illustrating filtering circuitry of the invention.

Referring to the drawings, an exemplary catheter 10 configured for use in a system for measuring or monitoring biological functions of a patient in accordance with the present invention is illustrated in FIGS. 1 and 2. Exemplary catheter 10 generally includes a body portion 12 which has a distal end 14 and a proximal end 16. A plurality of lumens 18 are formed in the body portion 12 longitudinally between the distal end 14 and the proximal end 16. The lumens are generally indicated by reference numeral 18 and specifically indicated by reference numeral 18 with an alpha suffix, i.e., 18a, 18b, 18c, . . . 18n, which is shown in FIG. 2. This alphanumeric numbering convention will be followed as appropriated herein.

Although exemplary catheter 10 may be configured to measure or monitor any desired biological function, the principles of the present invention are exemplified herein with a catheter configured to measure cardiac output of a patient. However, those skilled in the art will understand that the principles of the present invention may be readily modified and adapted to systems which measure and monitor other biological functions with catheters.

Exemplary catheter 10 includes a heating element 20 and a temperature sensor 22. The heating element is disposed between the distal end 14 and the proximal end 16 of the body portion 12, and the temperature sensor 22 is disposed between the heating element 20 and the distal end 14. Heating-element wires 24 and temperature-sensor wires 26 respectively extend from the heating element 20 and the temperature sensor 22 to the proximal end 26 of the body portion 22 within one of the lumens 28 or within respective lumens as shown. Each wire 24 and 26 may include a conductor 28 and an insulator 30.

Referencing FIG. 3, a preferred embodiment of the temperature sensor 22 of the catheter 20 is shown. The temperature sensor 22 may be received in a port 32 which is formed in the body portion 12, extending from an external surface of the body portion 12 to the lumen 18 in which the temperature-sensor wires 26 are positioned (i.e., lumen 28c). The temperature sensor 22 may have a pair of insulated leads (not shown) which are accessible to the temperature-sensor wires 26 through the port 32 and to which the temperature-sensor wires 26 are respectively connected. A protective coating 34 may be applied over the temperature sensor 22 within the port 32.

Exemplary catheter 10 of the present invention may include coupling apparatus 36 connected to the proximal end 16 of the body portion 12. Exemplary coupling apparatus 36 may include a plurality of lumens (not shown) corresponding to and in communication with the lumens 18 of the body portion 12. From the lumens of the coupling apparatus 36 may extend a plurality of coupling units 38. Each of the coupling units 38a, 38b, 38c, . . . 38n may include a lead 40 and a couple 42 which are configured for connecting with a respective complementary attaching means, for example, for measuring a specific cardiovascular function. For example, any number of the couple units 38 may be used for measuring various biological and cardiac functions, introducing fluids into the vascular system, or inflating a balloon disposed at the distal end 14 of the body portion 12, as known in the art.

One of the coupling units 38 is used in conjunction with the heating element 20 (for example, coupling unit 38b), and another one of the coupling units is used in conjunction with the temperature sensor 22 (for example, coupling unit 38c). Accordingly, the heating-element wires 24 extend from lumen 18b of the body portion 12, through a corresponding lumen of the coupling apparatus 36, and through lead 40b to couple 42b of coupling unit 38b. Similarly, the temperature-sensor wires 26 extend from lumen 18c of the body portion 12, through a corresponding lumen of the coupling apparatus 36, through lead 40c to couple 42c of coupling unit 38c.

With reference to FIG. 4, in use the catheter 10 is inserted into a patient 44 (which will be described in more detail below) and connected to processing instrumentation 46 which monitors and measures various cardiovascular functions of the patient. One of the biological and cardiovascular functions measured by the instrument 46 is cardiac output, which is measured based on signals from the temperature sensor 22. In accordance with the present invention, a signal-conditioning cable 50 is interdisposed between coupler 42c and the instrument 46. Exemplary cable 50 includes circuitry which conditions a signal provided by the temperature sensor 22 and then provides the conditioned signal to the instrument 46. As described above, in many instances cardiac output cannot be accurately measured by the instrument 46 in the presence of significant thermal and/or electrical noise. A preferred embodiment of the circuitry of exemplary signal-conditioning cable 50 reduces the amount of noise in the signal from the temperature sensor 22 so that the instrument 46 is able to accurately measure cardiac output.

Exemplary cable 50 includes an input connector 52 which is configured to releasably engage with the temperature-sensor coupler 42c and an output connector 54 configured to releasably engage with an input 55 of the instrument 46. Referencing FIG. 5, exemplary signal-conditioning cable 50 includes a conditioning circuit 56. As mentioned above, the temperature sensor 22 preferably includes a thermistor which is a resistive element indicated by $R_T$. Exemplary conditioning circuit 56 may include a capacitor 58 which, in combination with thermistor $R_T$, forms a passive RC circuit external to the catheter 10 and the instrument 46. Filter-configured conditioning circuit 56 may also include an inductor to form an RCL circuit. Exemplary filter circuit 56 attenuates both thermal noise from thermistor $R_T$ and high-frequency noise to a level which enables the instrument 46 to accurately calculate cardiac output, even in the presence of large amounts of noise, including noise associated with electrocautery (which is the process of making incisions with high-frequency current).

In addition to thermistor $R_T$, exemplary temperature sensor 22 may include a reference resistor $R_{ref}$ disposed at or near the proximal end 16 of the catheter 10. Reference resistor $R_{ref}$ is a normalizing and/or linearizing resistor for providing a constant resistance ratio with thermistor $R_T$ at a desired temperature, e.g., 37° C., as known in the art. In an exemplary embodiment of the invention, capacitor 58 may have a value of about 100 microfarads ($\mu f$), thermistor $R_T$ may have a value of about 14 kiloOhms (kΩ), and reference resistor $R_{ref}$ may have a value of about 10 kΩ. The values of capacitor 58, thermistor $R_T$, and reference resistor $R_{ref}$ may be any value depending upon the particular configuration of the catheter 10 and cable 50.

The single-pole low-pass filter defined by capacitor 58 in parallel with thermistor $R_T$ attenuates frequencies greater than a predetermined frequency. In many applications, this predetermined frequency is at least about 0.5 Hertz (Hz). The response time of thermistor $R_T$ is accordingly reduced, for example, to a point at which it may take about 0.8 second to reach about 63% of a final steady-state value. This reduction in response time allows thermistor $R_T$ to respond adequately to temperature changes.

A specific embodiment of signal-conditioning cable 50 is illustrated in FIG. 6. As shown, exemplary input connector 52 may include two input connectors 52a and 52b. For example, input connector 52a may be configured to be releasably engagable with one of the couplers 42 of the catheter 10, and input connector 52b may be configured to be releasably engagable with another one of the couplers 42 of the catheter 10. Exemplary output connector 54 may be configured as a nine-pin connector for releasably engaging with a complementary input 55 of the instrumentation 46. Signal-conditioning circuitry 50 is interconnected between input connector 52a and output connector 54 to condition the signal from the temperature sensor 22. As shown, exemplary circuitry 50 includes capacitor 58 which is configured to be in a parallel relationship with thermistor $R_T$ when input connector 52a is connected to the catheter 10.

Although illustrated and described as a component separate from the catheter 10 and the instrument 46, exemplary filter circuit 56 may be integrated into the catheter 10, either within the body portion 12 or within one of the coupling units 38, or into the instrument 46, if desired. In addition to the passive RC circuit illustrated in FIG. 5, exemplary conditioning circuit 56 may include high-pass filters, band-pass filters, and band-reject filters. Conditioning circuit 56 may also form an active filter to drive an operational amplifier circuit for signal filtering and other signal-conditioning operations.

The catheter 10 is illustrated in FIG. 5 in an exemplary use for measuring cardiac output, although the catheter can be used to measure any type of biological function. In use the body portion 12 of the catheter 10 may be inserted into the cardiovascular system of the patient 44 by making an incision in the patient and inserting the body portion 12 into a blood vessel of the patient. The body portion 12 is urged endovascularly until the distal end 14 is positioned at a target location with the temperature sensor 22 downstream of the heating element 20. The target location is preferably within the pulmonary artery 60 so that the cardiac output of the right ventricle of the heart 62 may be measured. As known in the art, the body portion 12 of the catheter 10 may be inserted either jugularly (as indicated at A) or femorally (as indicated at B). Jugular access leads the catheter 10 through the superior vena cava and into the right atrium of the heart 62. Femoral access leads the catheter 10 into the inferior vena cava and into the right atrium of the heart 62. Once in the right atrium, the distal end 14 may be urged into the right ventricle and through the pulmonary valve into the pulmonary artery 60.

With the body portion 12 positioned in the patient, the couple 42 corresponding to the heating element 20 (i.e., couple 42b) is connected to the instrument 46 for providing electrical signals to activate the heating element 20, as known in the art. The coupler 42 corresponding to the temperature sensor 22 (i.e., coupler 42c) is connected to the input connector 52 of exemplary cable 50, and the output connector 54 of the cable is connected to the input 55 of the instrument 46 which processes the conditioned signals from the temperature sensor 22. The conditioned signals from cable 50 are used to calculate blood temperature which, in turn, is used to calculate cardiac output of the patient 44. In operation the heating element 20 is activated, heating the volume of blood passing over and around the heating element 20. The resistance of the temperature sensor 22 changes from the heating of the blood, changing the signal received at the instrument 46. The instrument implements an algorithm to calculate cardiac output as known in the art. In the preferred embodiment of the catheter 10 in which the temperature sensor 22 includes thermistor $R_T$, the resistance of the thermistor decreases as the temperature of the blood increases.

Exemplary signal-conditioning cable 50 may be flexible and of any desired length. Alternatively, cable 50 may be configured as a plug-like interface connected between the catheter 10 and the instrumentation 46. As mentioned above, signal-conditioning cable 50 may include any combination or configuration of circuit elements, including capacitors, resistors, inductors, amplifiers, and so on, to perform any desired signal-conditioning function. One of the advantages of signal-conditioning cable 50 is that neither the catheter 10 nor the instrumentation 46 needs to be modified. Accordingly, the life-time of the instrumentation 46 may be extended. In addition, although the catheter 10 may be disposable after a single use, exemplary cable 50 may be reused as many times as desired.

In a commercial embodiment the catheter 10, the overall length of the body portion 12 may be any desired length suitable for measuring biological functions in a patient, which is preferably about 110 cm, thereby allowing the body portion 12 of the catheter 10 to be inserted into the patient femorally. An outer diameter of the body portion 12 is preferably about 7 French, although this diameter depends upon the number of lumens 18 formed within the body portion 12, the size of the lumens 18, and so on. The catheter 10 may have about five to seven lumens 18. The lumens 18, other than those used to house the heating-element and temperature-sensor wires 24 and 26, may be used for any purpose known in the art, for example, as an inflation lumen in conjunction with a balloon (not shown) disposed at the distal end 14 of the body portion 12. Catheter model Nos. 139, 746, and 757 available from the Edwards Critical Care division of Baxter International Corporation located in Irvine, Calif., are examples of multi-lumen catheters which may be used for the catheter of the present invention. Further, the catheter 10 may be configured with any suitable commercially available temperature sensor or thermistor.

A number of commercially available instruments which may be used to process the conditioned electrical signals from the temperature sensor 22 (via the signal-conditioning cable 50) to calculate blood temperature, blood flow, cardiac output, etc. Examples of the instrument 46 include COM1, COM2, SAT2, REF, Explorer®, and Vigilance®, each of which is available from Baxter Healthcare Corporation. FIG. 5 illustrates that exemplary instrumentation 46 includes circuit elements such as resistors R1, R2, and R3, amplifiers and/or buffers A1 and A2, a current source, and so on, as known in the art. These and other instruments may be used to practice the principles of the present invention for measuring various biological functions in addition to cardiac output.

Those skilled in the art will understand that the preceding exemplary embodiments of the present invention provide the foundation for numerous alternatives and modifications thereto. These other modifications are also within the scope of the present invention. Accordingly, the present invention is not limited to that precisely as shown and described herein.

What is claimed is:

1. A system for monitoring a biological function of a patient, said system comprising:
    a catheter including a temperature sensor disposed at or near a distal end thereof, said temperature sensor for providing a signal indicative of changes in temperature;
    a cable including an input connector for connecting to said catheter, an output connector, and circuitry connected between said connectors sensor for conditioning said signal from said temperature sensor; and
    instrumentation including an input for connecting to said output connector of said cable for processing said conditioned signal to determine the biological function.

2. A system as claimed in claim 1 wherein said temperature sensor of said catheter includes a thermistor.

3. A system as claimed in claim 2 wherein said circuitry of said cable includes a capacitor which is configured to form a filter circuit in conjunction with said thermistor.

4. A system as claimed in claim 3 wherein said filter circuit is a low-pass filter.

5. A system as claimed in claim 3 wherein said filter circuit attenuates frequencies greater than about 0.5 Hertz.

6. A system as claimed in claim 3 wherein:
    said thermistor has a value of about 14 kiloOhms; and
    said capacitor has a value of about 100 microfarads.

7. A system as claimed in claim 1 wherein said instrumentation processes said conditioned signal to determine cardiac output.

8. A cable for filtering a signal from a thermistor catheter and for providing a filtered signal to an instrument for processing to measure a biological function of a patient, said cable comprising:
    an input connector for attaching to the catheter;
    an output connector for attaching to the instrument; and
    circuitry interconnected between said input and output connectors for filtering the signal from the catheter and for providing a filtered signal to the instrument.

9. A cable as claimed in claim 8 wherein said circuitry includes a capacitor which is in a parallel configuration with a thermistor of the catheter when said input connector is attached to the catheter.

10. A cable as claimed in claim 8 wherein said input connector is releasably attachable to the catheter and said output connector is releasably attachable to the instrument.

11. A method for removing noise from a signal provided by a thermistor catheter to instrumentation for measuring a biological function of a patient, the signal including thermal and/or high-frequency noise, said method comprising:
    receiving the signal from the catheter;
    filtering the thermal and/or high-frequency noise from the signal; and
    providing the signal to the instrumentation.

12. A method for measuring a biological function of a patient, the patient having a cardiovascular system with a heart, said method comprising the steps of:
    providing a catheter with a temperature sensor for providing a signal;
    providing a signal-conditioning cable including circuitry for conditioning said signal from said temperature sensor;
    providing instrumentation for processing said signal to measure the biological function;
    providing access to the cardiovascular system of the patient;
    inserting said catheter into the cardiovascular system;
    positioning a distal end of the catheter at a target location;
    connecting said signal-conditioning cable to said catheter and said instrumentation.

13. A method as claimed in claim 12 wherein:
    said step of providing a catheter comprises the step of providing a catheter with a temperature sensor including a thermistor; and
    said step of providing a signal-conditioning cable comprises the step of providing a signal-conditioning cable including circuitry with a capacitor such that said capacitor is in a parallel configuration with said thermistor when said signal-conditioning cable is connected to said catheter.

14. A method as claimed in claim 12 wherein said step of providing instrumentation comprises the step of:
    providing instrumentation for processing said signal to measure cardiac output.

15. A system for monitoring a biological function of a patient, said system comprising:
    a catheter including a body portion with a distal end and a proximal end, a temperature sensor disposed at or near said distal end of said body portion, a coupler disposed at or near said proximal end of said body portion, a lumen formed within said body portion between said temperature sensor and said coupler, and wires connected to said temperature sensor and to said coupler and extending within said lumen, said wires for carrying a signal from said temperature sensor to said coupler;

an instrument for processing said signal to measure the biological function, said instrument including an input; and a signal-conditioning cable including an input connector for releasably engaging with said coupler of said catheter, an output connector for releasably engaging with said input of said instrument, and a filter circuit for receiving said signal from said temperature sensor, filtering said signal, and providing said signal to said instrument.

16. A system as claimed in claim 15 wherein said temperature sensor of said catheter includes a thermistor.

17. A system as claimed in claim 16 wherein said filter circuit includes a capacitor connected in parallel with said thermistor.

18. A system as claimed in claim 15 wherein said instrument processes said signal to measure cardiac output.

* * * * *